United States Patent [19]

Smith

[11] 4,443,215

[45] Apr. 17, 1984

[54] STERILE DOCKING PROCESS, APPARATUS AND SYSTEM

[75] Inventor: James G. Smith, Newark, Del.

[73] Assignee: E. I. Du Pont de Nemours & Company, Wilmington, Del.

[21] Appl. No.: 395,598

[22] Filed: Jul. 6, 1982

[51] Int. Cl.³ ............................................. A61M 5/00
[52] U.S. Cl. ...................................... 604/29; 604/283; 604/905; 156/502; 141/1
[58] Field of Search ......................... 604/29, 905, 283; 285/3, 4, 21; 156/502, 503, 86, 157; 141/1

[56] References Cited

U.S. PATENT DOCUMENTS 4,035,534 7/1977 Nyberg ................................ 156/86
4,251,310 2/1981 Goldhaber et al. ............ 604/272 X

*Primary Examiner*—Stephen C. Pellegrino

[57] ABSTRACT

A process, apparatus and system for making a sterile connection between two thermoplastic resin tubes is disclosed. The process comprises forming a continuous molten seal simultaneously between an end of a hot, multi-ended, hollow needle and a wall of each of said tubes, thereby providing fluid communication, and cooling said seals and needle. As the thermoplastic resin cools a sterile weld is formed.

23 Claims, 6 Drawing Figures

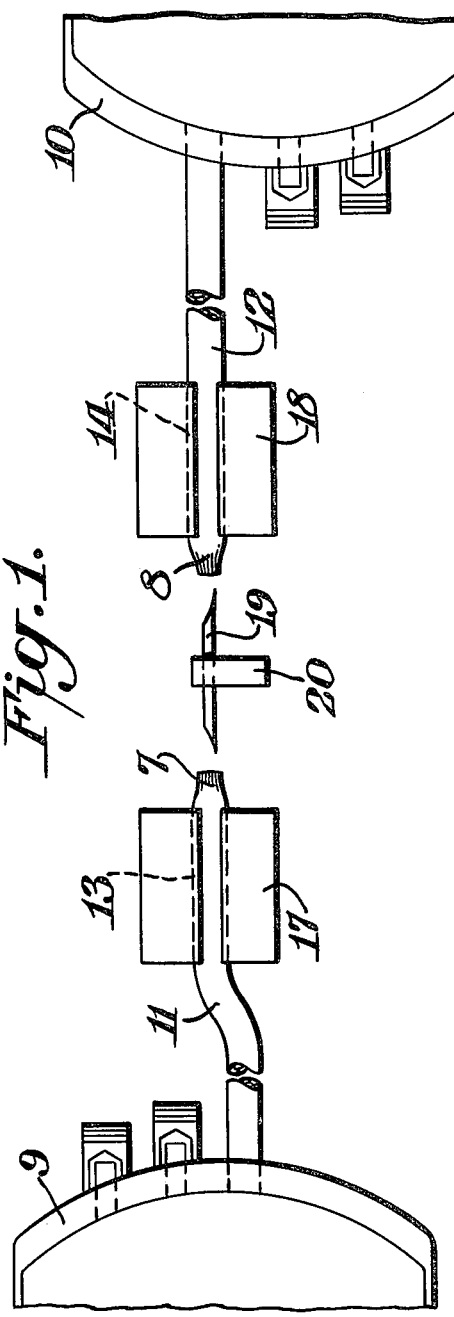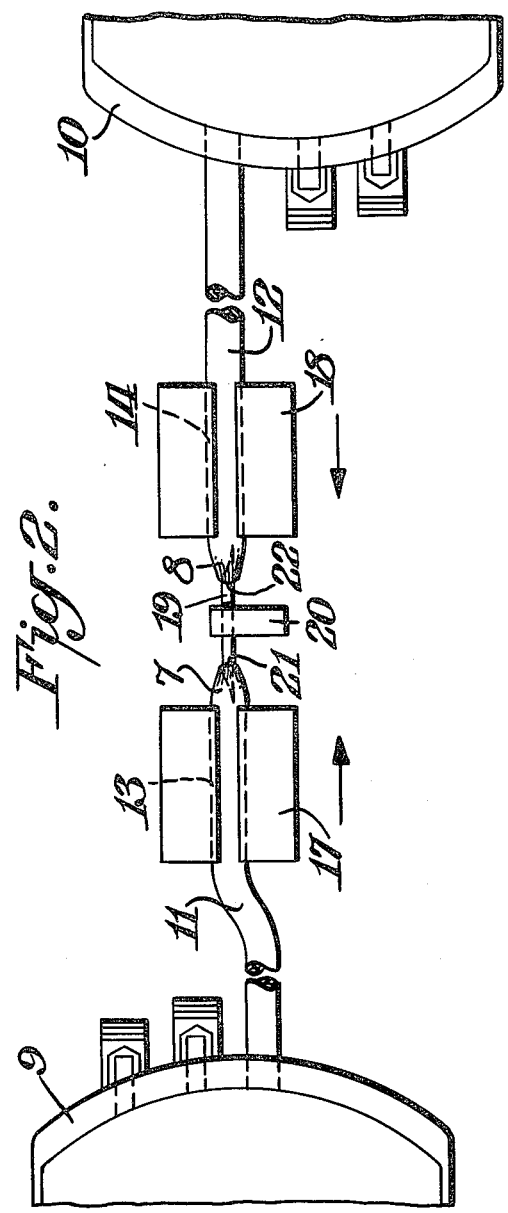

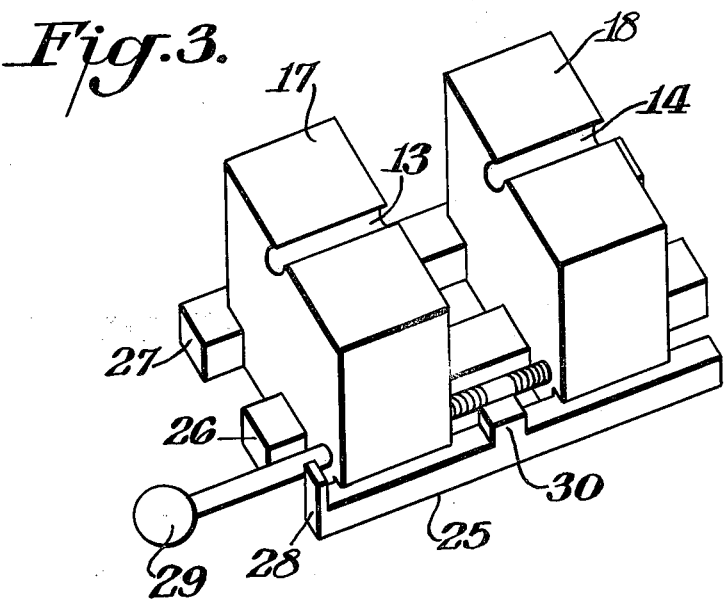
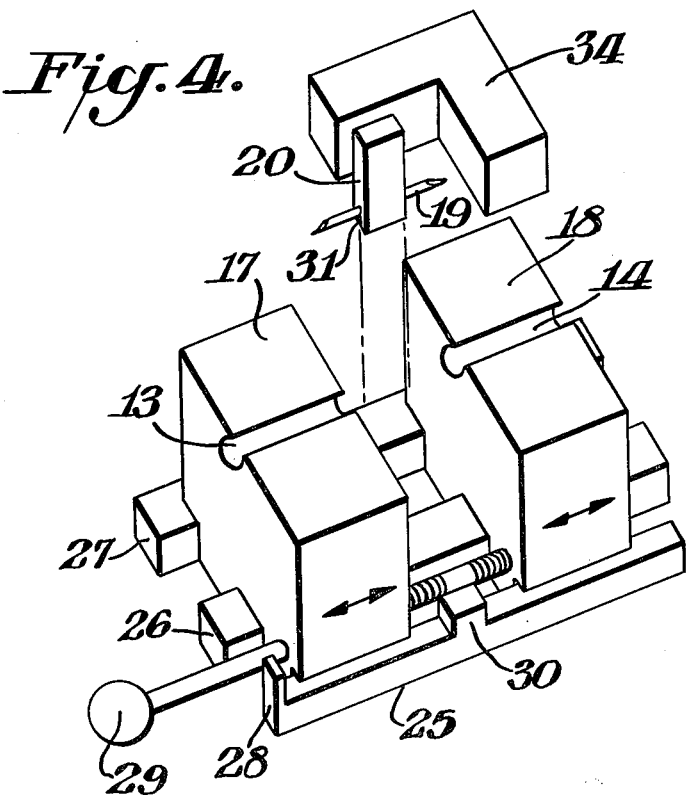

STERILE DOCKING PROCESS, APPARATUS AND SYSTEM

BACKGROUND OF THE INVENTION

1. Field of the Invention

This invention relates to a process, apparatus and system for forming a sterile connection (sterile docking) between two tubes.

At the present time there are a number of medical and scientific procedures which require the sterile transfer of fluids from one container to another. The only truly sterile transfer system in current use involves prejoining containers with tubes and then sterilizing the entire assembly. This is inflexible and costly since new containers cannot be added and the number of joined containers needed is often not known at the time of initial filling.

An example of the need for sterile docking is in continuous ambulatory peritoneal dialysis (CAPD). This procedure is replacing dialysis of blood outside the body in membrane diffusion cells where waste products normally removed by kidneys are washed from the blood, which is then returned to the patient. Dialysis outside of the body is a time-consuming procedure and sometimes results in damage to the blood by exposure to materials and conditions external to the body. In CAPD, the patient is required to spend time only for draining spent dialysate and replacing it with a fresh solution.

The CAPD patient has a tube connected to his or her peritoneal cavity via an implanted catheter. A tube from a bag of fresh dialysis solution is connected to the patient's tube. The fresh dialysis solution is drained from the bag into the patient's peritoneal cavity where it remains for about 3-4 hours. During this treatment period, the empty bag is folded and carried by the patient who can continue with his or her normal activities. After this treatment period, the spent dialysate is drained back into the empty bag which is then disconnected from the patient's tube. A bag of fresh dialysis solution is then connected to the patient's tube and the procedure is repeated. Connection to a new bag of dialysis solution exposes the tube ends to airborne bacteria or other contamination even though precautions are taken. No satisfactory way heretofore has existed to insure sterility in spite of the elaborate and costly precautions now employed including the use of masks, gloves, gauze strips and disinfectant solutions. Usually contamination does occur to the extent that a case of peritonitis is contracted perhaps on the average once or more a year and scar tissue from it inhibits dialysis.

Truly sterile connections could minimize the occurrence of peritonitis. Also any other treatment bags, such as for an antibiotic, bacteriostat, or other medication, could be connected as desired.

A similar need for sterile docking exists for blood bags. At present, blood from a donor is drawn into a primary bag which may be joined to one or two satellite bags, all connected and sterilized before use. These satellite bags may be needed for holding blood separated components, such as plasma or platelets; treating agents, such as bases, buffers, stabilizers for cell metabolism, other preservatives, or rejuvenants; or washes to remove a treating agent or other contaminant. Actually, it is not feasible to have preconnected bags for all the treatments which may be desired. Supplemental treatments such as fresh preservative cannot now be added sterilely during bag storage by any commercially acceptable procedure. In addition, to avoid the expense of unused satellite bags, the number of such bags is chosen based on limited, predicted needs. The inability to forecast needs well adds greatly to inventory requirements and complicates scheduling of blood donations.

Currently, very limited use is made of quality control as a time assay of the quantity and quality of components in separated blood factions. The main reason for the current limited use is that heretofore an entry into a sterile blood unit exposed the blood to bacteria, thereby requiring that the blood be used within 24 hours from entry. Hence, although the viability of stored blood components can be extended by supplemental treatments, such as adding a preservative during storage, such treatments are usually not effected.

Moreover, the primary blood bag contains anticoagulant which can be sterilized only by heat (steam); thus all preconnected bags are also sterilized by wet-sterilization techniques, i.e., steam or hot water in an autoclave apparatus. These bags are made of plasticized polyvinyl chloride (PVC), although other materials are known to be useful for constructing bags which are favorable for other reasons, such as greater oxygen permeability. Since many such materials, e.g., oxygen permeable polyethylene, are not steam sterilizable, they are not now used in preconnected systems.

A sterile docking means would permit one to effect whatever processing is desired without compromising sterility, limiting storage life or requiring the preconnection of a multitude of bags, all wet-sterilizable, without knowing which, if any, will be used.

2. References

U.S. Pat. No. 3,013,925 discloses a method of welding two joints of thermoplastic pipe wherein the inside of each end of the joints of pipe to be welded is beveled and the ends of the pipes are heated, for example by pressing the ends of the sections of pipe against a heated plate, after which the ends of the sections are forced together so that flow of softened material is to the outside of the pipe and a weld is effected substantially without formation of a bead on the inside of the welded pipe.

U.S. Pat. No. 3,035,631 discloses a tip for welding plastic parts. The tip has a knife edge at each of two opposing ends. One end of the knife is thick whereas the other is thin. The patent states that as the thin end passes through the joint, it will induce molten plastic surfaces to flow together.

U.S. Pat. No. 3,117,903 discloses a method of joining thermoplastic pipe without forming a troublesome inside ridge at the point of weld, said method involving the immersion of the ends of pipe to be welded in inert high boiling organic liquid heated above the softening temperature of the polymer forming the pipe. Thereby, the ends of the pipe are caused to expand and flare outwardly; then the pipe is withdrawn from the bath and the ends butted together.

U.S. Pat. No. 3,897,296 discloses a method of welding two plastic surfaces together by juxtapositioning the surfaces, heating the surfaces to a temperature approaching the flash point of the plastic surfaces to liquefy the surfaces, removing a portion of the liquefied surfaces to expose unoxidized surfaces therebeneath and immediately bringing the unoxidized surfaces into abutment with one another. The patent is silent as to cutting a tube as well as forming a sterile dock.

U.S. Pat. No. 3,968,195 discloses a method for making a sterile connection between two rigid tubes the free ends of which have thermoplastic diaphragms which seal them off. The free ends of each rigid tube are aligned while being spaced slightly apart, and each thermoplastic diaphragm is opened by heating. The free ends of the rigid tubes are then brought into contact and held in position under a slight pressure while the thermoplastic material cools and solidifies, thereby creating a permanent connection. This process requires tubes which have low-melting thermoplastic diaphragms on the ends which can only be used once, i.e., another connection to the same tubing cannot be made.

U.S. Pat. No. 4,209,013 discloses an improvement in a sterile connector system for continuous peritoneal dialysis in which a dialysis solution container having a transfer port is coupled to tubing extending from a patient's peritoneal cavity. The improvement comprises a flexible housing having a first area thereof for attachment to the transfer port and a second spaced area for attachment to the patient's tubing. The attachment areas define openings for enabling the transfer port and patient's tubing to extend within the interior of the flexible housing when they are attached thereto. The flexible housing has means for receiving a sterilizing fluid therein and is operable to enable the transfer port and the patient's tubing to be sterilized within the housing and also connected to each other within the housing.

U.S. Pat. No. 4,223,675 discloses a system for producing sterile, non-autoclavable body fluid containers having autoclaved liquid therein, comprising a dry-sterilized package formed of a material which is unsuitable for being subjected to autoclave conditions, said dry-sterilized package including a sterile communication with the interior of said package; an autoclavable dispenser constructed of an autoclavable substance and containing liquid which was sterilized within the dispenser, said dispenser including a sterile connector having an initially closed sterile aperture in sterile communication with the interior of the dispenser; said package sterile connector and said dispenser sterile connector being in mating engagement with each other.

"An Aseptic Fluid Transfer System for Blood and Blood Components", B. A. Myhre et al, Transfusion, Vol. 18, No. 5 pp. 546-552, Sept.-Oct. 1978, describes a process for heat sealing two aseptic fluid transfer system (AFTS) units together. The AFTS units contain a layer of Kapton ® film (an aromatic polyimide resin which is stable at relatively high temperatures). A pair of dies, one of which is flat and one of which has a raised "H" shaped area, are brought together under a pressure of 100 psi ($6.9 \times 10^6$ dynes per square centimeter) with the AFTS units disposed between the dies. The temperature of the dies is raised to 200° C. (392° F.) over a period of 45 seconds. The dies are withdrawn and upon removal of the AFTS units from the dies, the AFTS units are heat sealed together by a seal surrounding an opening between the AFTS units. Blood bags constructed with an AFTS unit attached can thereby be joined. This system is slow and requires specially constructed units that can only be used once.

Other patents directed to sterile connection apparatuses or methods include U.S. Pat. Nos. 4,157,723, 4,242,310 and 4,253,500.

SUMMARY

The present invention relates to a process, apparatus and system for joining sterile, closed end tubes or conduits using a hot multi-ended hollow needle means while maintaining system sterility. The hot needle is maintained at a temperature hot enough to kill bacteria with no chance for viable airborne or surface bacteria to find their way inside either of the tubes or the joint. The process comprises forming a continuous molten seal simultaneously between an end of a hot multi-ended, hollow needle and a wall of each of said tubes, thereby providing fluid communication, and cooling said seals and needle. This invention provides a quick, inexpensive system with no special fittings permitting maximum flexibility in processing, storing and using sterile fluids.

The apparatus of the invention comprises mounting blocks adapted to receive and hold tubes to be joined; a hollow, multi-ended needle; means for positioning said hollow needle in alignment to intersect where said blocks are adapted to receive said tubes or lying substantially coaxially therewith; means for heating said hollow needle; and means for urging said blocks and said needle partially together.

BRIEF DESCRIPTION OF THE DRAWINGS

FIG. 1 is a plan view of mounting blocks used to hold two tubes which are to be joined in the starting position.

FIG. 2 is a plan view of the two tubes being penetrated by a hot needle.

FIG. 3 is a perspective view of the mounting blocks slidably mounted on their guides.

FIG. 4 is a perspective view of the mounting blocks, slidably mounted on their guides and hollow needle with block heater.

DETAILED DESCRIPTION OF THE INVENTION

Figure 5:
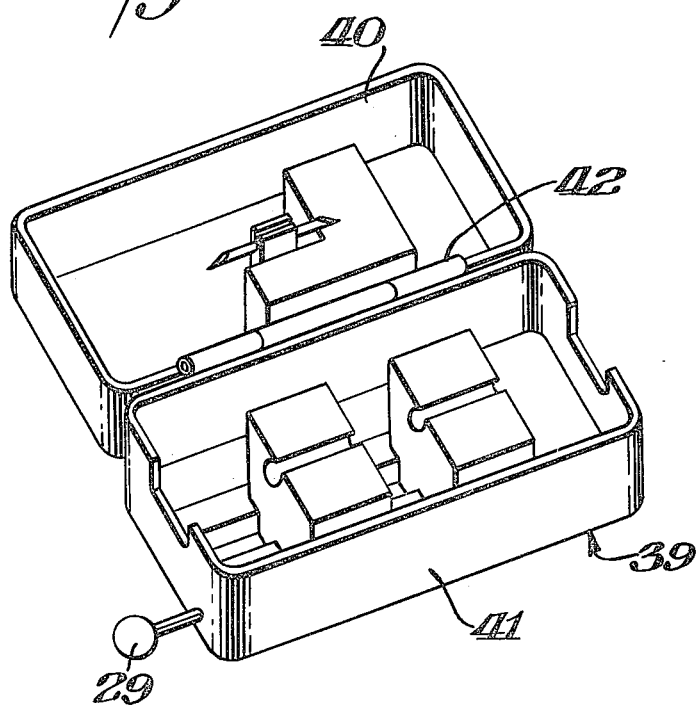
FIG. 5 is a perspective view of the mounting blocks fixedly arranged in a housing.

Referring now to FIG. 1 the sealed end 7 of thermoplastic tube 11 is inserted in slot 13, machined in block 17. The sealed end 8 of tube 12 is inserted in slots 14, machined in block 18. In FIGS. 1-2, tubes 11 and 12 are connected to blood bags 9 and 10. Alternately, one of said tubes may be connected to a dialysis bag and the other to the patient's peritoneal cavity. Also, the tube which is connected to the patient's peritoneal cavity may be connected at the other end to an empty bag in lieu of having a sealed end.

Referring now to FIG. 2, the two blocks 17 and 18 have been slid in the direction shown by the arrows, relative to hot needle, which in the figure is made of stainless steel, so that the hot needle has melted through tubes 11 and 12 and there are now two molten tube interfaces 21 and 22.

Referring now to FIG. 3, blocks 17 and 18 are shown in their initial position. The blocks are shown slidably mounted on guides 25, 26 and 27. FIG. 3 also shows operating handle 29 which is partially threaded in opposing directions so that when it is turned the blocks move toward each other. Stop 30 serves to limit the extent to which the blocks can be urged together while stop 28 serves to limit motion of the blocks when the handle 29 is turned to move the blocks away from each other. Operation of this embodiment is best described by using FIGS. 3-5 along with reference to FIGS. 1 and 2 already described. The operator inserts tube ends in slots 13 and 14 as shown in FIG. 1. The hollow double-ended needle 19 and cartridge heater 20 shown in FIG. 4 are lowered so that needle 19 is positioned between mounting blocks 17 and 18 in coaxial alignment with the slots in said mounting blocks. This positioning is effected by having cartridge heater 20 fixedly attached to block 34 which is in the upper portion 40 of housing 39 shown in FIG. 5 and the mounting blocks, stop-blocks 28 and 30 and the accompanying slides fixedly arranged in a base portion 41 of housing 39 so that when the housing is closed the needle is properly situated. The two sections of the housing are attached by hinge 42. Needle 19 is mechanically fitted into slot 31 of cartridge heater 20.

Cartridge heater 20 is activated. The operator turns handle 29 which moves blocks 17 and 18 together on slides 25, 26 and 27, thereby urging the tubes onto hot needle 19 as shown in FIG. 2. The blocks strike stop-block 30 which thus limits to extent to which needle 19 penetrates the tubes. Cartridge heater 20 is deactivated. The operator removes the joined tubes after about 5 seconds' delay for the joints to cool.

Figure 6:
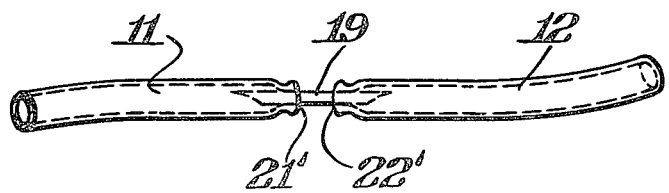
FIG. 6 is a perspective view of the joined tubes.

Referring now to FIG. 6, tubes 11 and 12 are shown joined by needle 19 at fused interfaces 21' and 22' to provide fluid communication between the tubes.

The hollow needle can be made from stainless steel, ceramic material, or any other inert high melting-point material. The multi-ended hollow needle can take many forms, such as Y-shaped or U-shaped, and can have two or more ends, but preferably is double-ended. Although the apparatus of the invention has been described in detail with respect to the double-ended needle mode, modifications necessary to effect other modes are not difficult to envision. The needle can have an outer diameter of about 100% of the inner diameter of the tube it is to be inserted into. The inner diameter of the needle should not be so small as to unduly restrict flow of liquid within the tube and should be greater than 0.125 inch (0.32 mm). An inner diameter of 0.125 inch or less increases significant chances that the tip of the needle will become clogged with polymer. The hollow needle should have thin walls, e.g., the inner diameter should be nearly equal to the outer diameter of the needle, so that rapid cooling of the needle will occur when the heater is deactivated. In the embodiment in FIG. 4 the needle is heated through conduction by cartridge heater 20 which in turn is heated by electrical resistance. However, various other heating means can be used to heat the needle such as electrical resistance, induction, dielectric heating, high frequency heating, radiation from a heat source, etc., depending on the material from which the needle is constructed.

Currently-used blood and dialysis bags and tubes are made of plasticized polyvinyl chloride for flexibility, strength and steam sterilizing. Generally, for these plasticized polyvinyl chloride tubes, the needle will be heated to a temperature of from about 500° F. (260° C.) to 750° F. (399° C.) which is also suitable for most other thermoplastic tubing. The needle preferably is at a temperature high enough (1) to kill rapidly (less than one second) any bacteria or bacterial spores on the outside surface of the tubes and (2) to melt rapidly the thermoplastic resin from which the tubes are formed. The tubes are heat-sealed closed at their ends or connected to a bag. The tubes and whatever bag or bags they are connected to will have been sterilized. Below about 500° F. (260° C.) bacteria and bacterial spores are not rapidly killed by the heat from the severing means. Above about 750° F. (399° C.) most polymers such as plasticized polyvinyl chloride or polyolefins such as polypropylene or polyethylene begin to become too liquid to maintain a seal with the needle. About 600° F. (316° C.) is the preferred temperature for use with conventional plasticized polyvinyl chloride blood bag tubing. Another upper limit is the temperature where the resin from which the tube is made begins to degrade in the time it is exposed to the heated hollow needle (about 2 seconds). For plasticized polyvinyl chloride and polyolefins the upper limit is about 300° F. (149° C.) above the melting point of the thermoplastic resin from which the tube is made.

Each tube should be advanced onto the needle at a rate such that the polymer from which each tube is fabricated melts up against the needle and there should be no mechanical rupturing of unmolten polymer or significant visible deformation of the tube. Excessive heating times are to be avoided in order to minimize excess melting or degradation of the polymer. For conventional 165 mil (4.2 mm) outside diameter, 10 mils (0.25 mm) thick wall plasticized polyvinyl chloride blood bag tubing, a time of 0.5 to 1.5 seconds for advancing the needle into the two tubes has been found to be most satisfactory. Cooling of the tubes and needle takes about 5–10 seconds and the tubes are then removed from the blocks. The cooling time depends in general on the needle size, thickness and material of construction.

The mounting blocks are made of heat conductive metal and serve as heat sinks to assist rapid cooling of the joint. The space between the blocks and the needle is not critical.

The tubing used should be formed of a thermoplastic resin which melts at least 50° F. below the temperature at which it begins to degrade in the time it is exposed to heat in the process of the present invention. The tubes to be connected can have different diameters. The tubes to be joined can be made of the same material or can be made of different resins. The resin from which the tubes are made must be capable of wetting the needle material so as to form a permanent seal when cooled.

In order to obtain a secure dock, tubes to be joined must not contain more liquid than a thin film on the walls at or near the locations where they are to be pierced and joined. Generally, the length of tubing which is empty of liquid need not be more than about 0.5 to 1 inch (13–25 mm). When either tube is connected to a container which contains spent liquid, the tube is heat sealed shut by a Hemitron ® device below the needle connection and then the unwanted bag is removed by cutting the tube below the heat seal. Subsequent docks to the same tube can be effected by heat sealing the tube with a Hemitron ® device, cutting off the section of the tube bearing the needle so as to leave the tube with a freshly sealed end and then accomplishing the dock with a new needle and second tube, also having a heat sealed end, as hereinbefore described. The tubes can be connected end to end or sidewall to sidewall. When the tubes are to be connected end to end, the double-ended hollow needle is positioned so that its longitudinal axis is substantially coaxial with the longitudinal axes of the slots in the tube mounts. When the tubes are to be connected side to side, the needle is positioned so that it is between the blocks and intersects where the blocks are adapted to receive the tubes.

The apparatus of the invention can form part of a sterile connection system for continuous ambulatory peritoneal dialysis in which a dialysis solution container with a transfer port that includes a segment of tubing is coupled to a tube extending from an implanted catheter opening into a patient's peritoneal cavity. In this embodiment of the invention the patient's tube and/or the transfer tube can have an entry port with a protective cover or a sealed distal end but preferably both have a sealed distal end. This system minimizes the possibility of peritonitis and permits any other treatment bag, such as a bag of antibiotic, bacteriostat, or other medication to be connected as desired. Moreover, this embodiment offers the additional advantage of eliminating the need for the patient to carry the empty dialysis solution bag because the bag can be sterilely disconnected and the patient's tube can be joined to a sterile sealed-end tube. It also eliminates the need for the present laborious procedure used to achieve sterility.

In another embodiment, the apparatus of the invention forms part of a sterile connection system for connecting two blood bags. One of the bags can be a donor bag and the other a transfer bag. The donor bag will have a blood collection tube and optionally can have a transfer port with a transfer tube. The transfer bag has a transfer tube (connection tube). The two bags can be sterilely connected by joining the connection tube of the transfer bag to the transfer port of the donor bag. The transfer port of the donor bag can be a conventional entry port, e.g., having a protective covering and a septum inside the port. The bags can also be connected by joining the blood collection tube of the donor bag to the connection tube of the transfer bag. In another embodiment, the blood collection tube and the connection tube of the transfer bag both have a sealed distal end.

In the preferred embodiment for both the blood bag system and the CAPD system, the donor bag and dialysis bag have, specifically for sterile connection, an additional tube (pigtail) which is connector-free and has a sealed distal end. The term "connector-free" as used herein means the tube does not bear any of the conventional fittings, such as a plastic fitting with a diaphragm, a low-melting thermoplastic insert, an insert fusable by radiant energy, or the like. The tube has a sealed distal end which is prepared solely by sealing the tube end together by use of heat, solvent or the like. This modified bag is further described in copending U.S. application Ser. No. 267,291, the relevant disclosure of which is incorporated herein by reference. The tube is equipped with means, such as a clamp, to prevent undesired flow of liquid into said tube.

In the present system for the sterile connection of blood bags, the need to pre-assemble bags into a system is eliminated. It is to be understood that the expression "blood bag" as used herein refers collectively to either the donor (primary) bag or the satellite bag. With the present invention satellite bags can be sterilely connected to a donor bag as the need arises. The donor bag can be made from a wet-sterilizable material, such as polyvinyl chloride whereas the satellite bags do not have to be wet-sterilizable but can be made of material which can be sterilized only by dry-sterilization means, such as irradiation or ethylene oxide treatment. For example, the satellite bag can be constructed from $O_2$ permeable polyethylene which would increase platelet viability. Alternatively, the satellite bag can be made from a polyethylene copolymer, a polyethylene laminate, polypropylene, or any other material. Supplemental treatments can be sterilely added and washing to remove treating agents can be sterilely effected. Some practitioners believe hepatitis risks can be reduced by washing red cells without previous freezing.

The sterile docking apparatus of the invention can also be used to provide a system for producing sterile, non-autoclavable body fluid containers having wet-sterilized (autoclaved) liquid therein. The system is similar to that described in U.S. Pat. No. 4,223,675; however, the present apparatus eliminates the need to have special connectors attached to the tubing.

With the present invention a dry-sterilized package can be formed from a synthetic resin material which is unsuitable for being subjected to wet-sterilization conditions but is particularly suitable for prolonged storage of body fluids. The autoclavable liquid is placed in an autoclavable dispenser equipped with an access tube which can then be heat-sealed closed. The dispenser package and liquid are then wet-sterilized in an autoclave. The dispenser package is next sterilely connected to a dry-sterilized container by using the apparatus and process of the invention. The dry-sterilized container can be equipped with a connector-free tube having a sealed distal end, said tube being specifically for sterile connection. After the sterile connection is made the autoclaved liquid is transferred to the dry-sterilized container which is non-autoclavable. If desired, the two containers can be separated by heat sealing the connecting tube while moving the containers apart so that each container is left with a connector-free tube having a sealed distal end. Other packages can be connected to either container by subsequent sterile docking operations. The autoclavable liquid can be an anticoagulant and the autoclavable dispenser package can be constructed from polyvinyl chloride. The non-autoclavable container can be a blood bag constructed from materials such as those previously described herein.

The process of the invention for joining two or more thermoplastic tubes together comprises forming a continuous molten seal simultaneously between an end of a hot, multi-ended, hollow needle and a wall of each of said tubes, thereby providing fluid communication, and cooling said seals and needle. The term "wall" as used herein means the sealed end or sidewall of the tubing. The process of the invention can be carried out using the hereindescribed specific embodiment of the apparatus of the invention but is not limited thereto. The conditions of operations are those previously set forth herein. Preferably, two tubes are joined with a double-ended, hollow needle.

I claim:

1. A process of joining at least a first and a second closed thermoplastic tube together comprising forming a continuous molten seal simultaneously between an end of a hot, multi-ended, hollow needle and a wall of each of said tubes, thereby providing fluid communication, and cooling said seals and needle.

2. A process of joining a first and a second closed thermoplastic tube together comprising forming a continuous molten seal simultaneously between an end of a hot, double-ended, hollow needle and a wall of each of said tubes, thereby providing fluid communications, and cooling said seals and needle.

3. A process of forming a sterile connection between a first tube and a second tube, both formed of a thermoplastic resin, comprising (a) mounting said tubes in a pair of spaced-apart mounting means; (b) urging a hot, double-ended, hollow needle simultaneously through a wall of each of said tubes at a rate such that the thermoplastic resin from which said tubes are formed and which is in contact with the ends of said needle becomes molten, whereby a molten interface is formed between a needle end and a wall of each of said tubes and fluid communication is provided; and (c) cooling the interfaces and needle whereby a sterile connection is formed between said tubes.

4. A process according to claim 3 wherein the hot, double-ended, hollow needle is maintained at a temperature above about 260° C. during step (b).

5. A process according to claim 4 wherein the hot, double-ended, hollow needle is maintained at a temperature below the temperature where the thermoplastic resin from which the tubes are made begins to degrade in the time used.

6. A process according to claim 5 wherein the tubes are mounted in a substantially parallel position and the hot needle is urged through a side wall of each tube.

7. A process according to claim 5 wherein each tube has a sealed distal end; the tubes are mounted end to end; and the hot needle is urged through the sealed distal end of each tube.

8. A process according to claim 6 or 7 wherein the mounting means holding the tubes are a pair of blocks having slots therein which hold said tubes.

9. A apparatus for forming a sterile connection comprising
mounting blocks adapted to receive and hold tubes to be joined;
a hollow, multi-ended needle;
means for positioning said hollow needle in alignment to intersect where said blocks are adapted to receive said tubes or lying substantially coaxially therewith;
means for heating said hollow needle; and
means for urging said blocks and said needle partially together.

10. An apparatus for forming a sterile connection comprising
a pair of spaced-apart mounting blocks adapted to receive and hold two tubes to be joined;
a hollow double-ended needle;
means for positioning said hollow needle between said blocks and aligned to intersect when said blocks are adapted to receive said tubes or lying substantially coaxially therewith;
means for heating said hollow needle; and
means for urging said blocks and said needle partially together.

11. An apparatus according to claim 10 wherein said hollow needle lies substantially coaxially to where said blocks are adapted to receive said tubes.

12. An apparatus according to claim 10 wherein said hollow needle is aligned to intersect where said blocks are adapted to receive said tubes.

13. A sterile connection system for continuous ambulatory peritoneal dialysis in which a dialysis solution container with a transfer port that includes a segment of tubing is coupled to a tube extending from a patient's peritoneal cavity, wherein the improvement comprises a pair of spaced-apart mounting blocks adapted to receive and hold the transfer port tube and the patient's tube; a hollow, double-ended needle; means for positioning said hollow needle between said blocks and aligned to intersect where said blocks are adapted to receive said tubes or lying substantially coaxially therewith; means for heating said hollow needle; and means for urging said blocks and said hollow needle partially together.

14. A sterile connection system according to claim 13 wherein the patient's tube is connector-free and has a sealed distal end.

15. A sterile connection system according to claim 14 wherein the transfer port tube is connector-free and has a sealed distal end.

16. A sterile connection system for joining two blood bags, each bag having a tube which can be used for connection and sterile connection being made by joining said tubes, wherein the improvement comprises a pair of spaced-apart mounting blocks adapted to receive and hold the tubes to be joined; a hollow, double-ended needle; means for positioning said hollow needle between said blocks and aligned to intersect where said blocks are adapted to receive said tubes or lying substantially coaxially therewith; means for heating said hollow needle; and means for urging said blocks and said hollow needle partially together.

17. A sterile connection system according to claim 16 wherein one of the bags is a donor bag and its blood collection tube is one of the tubes to be joined.

18. A sterile connection system according to claim 17 wherein the blood collection tube has a sealed distal end.

19. A sterile connection system according to claim 18 wherein the second bag is a transfer bag having a transfer port with a transfer tube and the transfer tube is the other tube to be joined.

20. A sterile connection system according to claim 19 wherein the transfer tube has a sealed distal end.

21. A sterile connection system according to claim 16 wherein one of the bags is a donor bag having, in addition to its blood collection tube, a connector-free tube to be used specifically for sterile connection, said tube having a sealed distal end.

22. A sterile connection system according to claim 21 wherein the donor bag is steam sterilizable and the other bag is a transfer bag made from material which is dry sterilizable only.

23. A sterile connection system according to claim 22 wherein the transfer bag has a connector-free tube having a sealed distal end.

* * * * *